United States Patent
Murthy

(10) Patent No.: US 7,550,625 B2
(45) Date of Patent: Jun. 23, 2009

(54) ESTERS OF FLORFENICOL

(75) Inventor: Yerramilli V. S. N. Murthy, Apex, NC (US)

(73) Assignee: IDEXX Laboratories, Westbrook, ME (US)

(*) Notice: Subject to any disclaimer, the term of this patent is extended or adjusted under 35 U.S.C. 154(b) by 0 days.

(21) Appl. No.: 12/250,238

(22) Filed: Oct. 13, 2008

(65) Prior Publication Data

US 2009/0105337 A1    Apr. 23, 2009

Related U.S. Application Data

(60) Provisional application No. 60/960,923, filed on Oct. 19, 2007.

(51) Int. Cl.
*C07C 229/28* (2006.01)
*C07C 69/66* (2006.01)
*A61K 31/22* (2006.01)
*A01N 37/12* (2006.01)
*A01N 37/44* (2006.01)

(52) U.S. Cl. .................. 560/155; 560/186; 560/187; 514/546; 514/551

(58) Field of Classification Search .............. None
See application file for complete search history.

(56) References Cited

U.S. PATENT DOCUMENTS

| | | | |
|---|---|---|---|
| 4,235,892 A | 11/1980 | Nagabhushan | |
| 4,311,857 A | 1/1982 | Nagabhushan | |
| 4,361,557 A | 11/1982 | Nagabhushan | |
| 4,382,892 A | 5/1983 | Hayakawa et al. | |
| 4,743,700 A | 5/1988 | Jommi et al. | |
| 4,876,352 A | 10/1989 | Schumacher et al. | |
| 5,082,863 A | 1/1992 | Apelian et al. | |
| 5,158,948 A | 10/1992 | Schoenleber et al. | |
| 5,336,664 A | 8/1994 | Camaggi et al. | |
| 5,352,832 A | 10/1994 | Wu et al. | |
| 5,382,673 A | 1/1995 | Clark et al. | |
| 5,476,854 A | 12/1995 | Young | |
| 5,556,829 A | 9/1996 | Camaggi et al. | |
| 5,574,020 A | 11/1996 | Klink et al. | |
| 5,663,361 A | 9/1997 | Towson et al. | |
| 5,723,447 A | 3/1998 | Macy et al. | |
| 5,756,506 A | 5/1998 | Copeland et al. | |
| 5,807,830 A | 9/1998 | Morozov et al. | |
| 5,866,549 A | 2/1999 | Or et al. | |
| 5,883,115 A | 3/1999 | Santus et al. | |
| 5,958,888 A | 9/1999 | Macy et al. | |
| 5,977,133 A | 11/1999 | Fung et al. | |
| 6,110,905 A | 8/2000 | Patterson et al. | |
| 6,140,374 A | 10/2000 | May et al. | |
| 6,239,112 B1 | 5/2001 | Macy et al. | |
| 6,310,053 B1 | 10/2001 | Patterson et al. | |
| 6,403,057 B1 | 6/2002 | Schneider et al. | |
| 6,660,278 B1 | 12/2003 | Larsson et al. | |
| 6,710,068 B2 | 3/2004 | LaColla et al. | |
| 2002/0028875 A1 | 3/2002 | Anderie et al. | |
| 2002/0065198 A1 | 5/2002 | Highsmith et al. | |
| 2003/0216447 A1 | 11/2003 | Kohan et al. | |
| 2003/0220302 A1 | 11/2003 | Kohan et al. | |
| 2004/0082553 A1 | 4/2004 | Boojamra et al. | |
| 2004/0198704 A1 | 10/2004 | Shuster et al. | |
| 2006/0014743 A1 | 1/2006 | Boojamra et al. | |

FOREIGN PATENT DOCUMENTS

| | | |
|---|---|---|
| EP | 0 014 437 | 8/1980 |
| WO | WO 0241899 | 5/2002 |
| WO | WO 03/077828 | 9/2003 |

OTHER PUBLICATIONS

Database CAPLUS on STN, Acc. No. 2005:612097, Hecker et al., WO2005063257 (Jul. 14, 2005) (abstract).*

A.D. Tuttle et al., "Bone Marrow Hypoplasia Secondary to Florfenicol Toxicity in a Thomson's Gazelle" (Bazella thomsonii), Journal of Veterinary Pharmacology and Therapeutics, vol. 29, pp. 317-319 (Aug. 2006).

R.H.C. Penny et al., "Effects of Chloramphenicol on the Haemopoietic System of the Cat," British Veterinary Journal, vol. 123, p. 145-153 (1967).

A.D.J. Watson, "Further Observations on Chloramphenicol Toxicosis in Cats," American Journal of Veterinary Research, vol. 41, p. 293-294 (Feb. 1980).

Bundgaard, "Design of Prodrugs", p. 7-9, 21-24, Elseiuer, Amsterdam, 1985.

Maier, et al.; "Separation of Enantiomers needs, challenges, perspectives", Journal of Chromatography, 2001; vol. 906, p. 3-33.

F.E. Hahn, Antibiotics, Ed. Gottlieb and Shaw, Springer-Verlag, New York, p. 308 (1967).

(Continued)

*Primary Examiner*—Brian J Davis
(74) *Attorney, Agent, or Firm*—Townsend & Townsend & Crew

(57) ABSTRACT

The invention relates to compounds of formula (I):

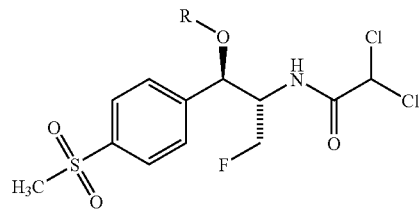

wherein R is —C(O)CH$_2$OCH$_2$CH$_2$OCH$_3$ or —C(O)CH$_2$N(CH$_3$)$_2$. The invention also relates to pharmaceutical compositions comprising a compound formula (I) and methods of treating or preventing a condition in an animal comprising administering to an animal in need thereof a compound of formula (I).

20 Claims, No Drawings

OTHER PUBLICATIONS

F.E. Hahn et al., Antibiotics and Chemotherapy, 6, No. 9, 531 (1956).
Cima et al., Il Farmaco, Ed. Sc. 12, No. 6,535 (1957).
S. Mitsuhashi et al., Jap J. Microbiol. 13, No. 2, 177-80 (1969).
M. Kono et al., Jap J. Microbiology 15(3), 219-27 (1971).
Office Action issued in related U.S. Appl. No. 11/700,069, filed Feb. 23, 2009.

* cited by examiner

ESTERS OF FLORFENICOL

CROSS REFERENCE TO RELATED APPLICATIONS

This application claims the benefit of U.S. Provisional Application Ser. No. 60/960,923, filed Oct. 19, 2007, currently pending.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention relates to esters of florfenicol that have advantageous properties compared to florfenicol itself and other esters of florfenicol, pharmaceutical compositions comprising the esters of florfenicol, and methods of treating or preventing a condition in an animal comprising administering to an animal in need thereof the esters of florfenicol.

BACKGROUND OF THE INVENTION

The chemical structure of florfenicol is:

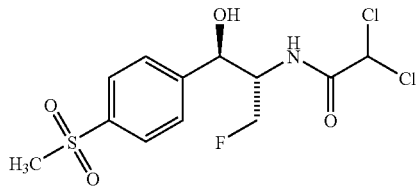

Florfenicol is an antibacterial agent that is a structural analog of chloramphenicol and thiamphenicol. Florfenicol, however, unlike chloramphenicol and thiamphenicol, has a fluorine atom instead of a hydroxyl group at the C-3 position of the core structure. Bacterial resistance to chloramphenicol and thiamphenicol is usually attributed to acetylation of the 3' hydroxyl group by the action of chloramphenicol acetyl transferase. Since florfenicol does not possess the 3' hydroxyl group, such a mechanism of inactivation is not possible with florfenicol, thus making florfenicol a highly useful antibiotic.

Florfenicol is active against a variety of microorganisms including *Citrobacter, Proteus mirabilis, Proteus* sp., *Shigella, Salmonella, Providencia, Bacteroides, Staphylococcos aureus, Enterococci, Pasteurlla haemolytica, Pasteurella multocida, Haemophilus somnus,* and *Haemophilus influenza.* Conversely, *Serratia marcescens, Pseudomonas aeruginosa,* and *Acinetobacter,* have been found to be resistant to florfenicol. Literature suggests that typical minimum inhibitory concentrations ("MICs") of florfenicol for various bacteria range from 0.3-1 μg/mL.

Dosage schedules for antibiotics are designed to maintain serum or tissue levels above the MIC for the target organism for a period of time sufficient to clear the infection. Drugs that are cleared rapidly must be administered in multiple doses to maintain effective levels. For example, the commercially available florfenicol composition, NUFLOR™, when used to treat a bacterial infection in cattle, is indicated for administration by intramuscular injection on day 0 followed by a second administration on day 2. Such multiple dosing is inconvenient.

US published application no. 2005/0041428 discloses esters of florfenicol, wherein the hydroxyl group has been esterified. The published application discloses that the esters, when administered to cattle, provide a florfenicol level in the blood serum of the animal that has a different $T_{1/2}$ and $C_{max}$ compared to florfenicol.

EP 0 014 437 discloses a large genus of compounds that encompasses florfenicol and alkyl esters of florfenicol.

There remains a need in the art, however, for compounds that, when administered to an animal, provide a therapeutically effective level of florfenicol in the blood serum of the animal for a sufficiently long period of time to avoid having to be administered multiple times to treat an infection and, in particular, to avoid administration by multiple injections. Multiple administration is inconvenient. The present invention addresses this need as well as other needs in the art.

SUMMARY OF THE INVENTION

The invention is directed to a compound of formula (I):

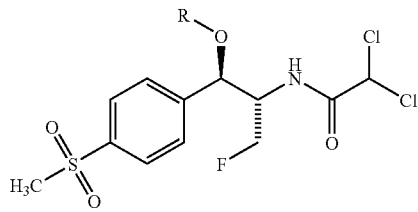

wherein R is —C(O)CH$_2$OCH$_2$CH$_2$OCH$_3$ or —C(O)CH$_2$N(CH$_3$)$_2$.

The invention is also directed to pharmaceutical compositions comprising the compound of formula (I) and a pharmaceutically acceptable excipient and to methods of treating or preventing a bacterial infection in an animal comprising administering to the animal a compound of formula (I).

DETAILED DESCRIPTION OF THE INVENTION

The invention is directed to a compound of formula (I):

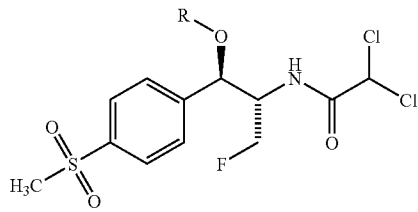

wherein R is —C(O)CH$_2$OCH$_2$CH$_2$OCH$_3$ or —C(O)CH$_2$N(CH$_3$)$_2$.

Definitions

The term "prodrug," as used herein means a chemical compound that is transformed in vivo to provide florfenicol, typically through the action of one or more enzymes. The prodrug is formed by derivatizing the alcohol functional group of florfenicol to provide an ester group.

The term "carboxylic acid," as used herein, means a carboxylic acid of formula $R^1$—C(O)OH, wherein $R^1$ is a $C_1$-$C_{22}$ hydrocarbon group.

The phrase a "$C_1$-$C_{22}$ hydrocarbon group," as used herein, means a straight or branched, saturated or unsaturated, cyclic or non-cyclic, carbocyclic group having from 1 to 22 carbon atoms. Similarly, phrases, such as a "$C_6$-$C_{16}$ hydrocarbon group," have a similar meaning. Thus, the phrase "$C_6$-$C_{16}$ hydrocarbon group" means a straight or branched, saturated or unsaturated, cyclic or non-cyclic, carbocyclic group having from 6 to 16 carbon atoms.

The term "salt," as used herein, means two compounds that are not covalently bound but are chemically bound by ionic interactions.

The term "condition," as used herein, means an interruption, cessation, or disorder of a bodily function, system, or organ. The condition can be, for example, a bacterial infection. The condition can be, for example, inflammation.

The phrase "treating," "treatment of," and the like, as used herein, means the amelioration or cessation of a specified condition.

The phrase "preventing," "prevention of," and the like, as used herein, means the avoidance of the onset of a condition.

The term "effective amount," as used herein, means an amount sufficient to treat or prevent a condition in an animal.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human.

The term "pharmaceutically acceptable," as used herein, when referring to a component of a pharmaceutical composition, means that the component, when administered to an animal, does not have undue adverse effects such as excessive toxicity, irritation, or allergic response commensurate with a reasonable benefit/risk ratio. Accordingly, the term "pharmaceutically acceptable excipient," as used herein, means an excipient that when administered to an animal does not have undue adverse effects such as excessive toxicity, irritation, or allergic response commensurate with a reasonable benefit/risk ratio. Similarly, the phrase "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA").

The term "pharmaceutically acceptable salt of a compound of formula (Ib)," as used herein, means a salt formed between a pharmaceutically acceptable acid and the basic amine group of the compound of formula (Ib). Illustrative salts include, but are not limited, to sulfate, citrate, acetate, oxalate, chloride, bromide, iodide, nitrate, bisulfate, phosphate, acid phosphate, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate ( i.e., 1,1'-methylene-bis-(2-hydroxy-3-naphthoate)) salts.

The phrase "pharmaceutically active compound," as used herein, means a compound that causes a pharmacological effect in an animal. Typically, the pharmacological effect is treating or preventing a condition in an animal.

The phrase "acidic pharmaceutically active compound," as used herein, means a pharmaceutically active compound that has an acidic functional group, i.e., a group that is capable of donating a proton to a basic functional group such as an amine group. Representative acidic functional group include, but are not limited to —COOH (i.e., carboxylic acid groups), —S(O)$_2$—OH (i.e., sulfonic acid groups), —OP(O)(OR)(OH), —O(P)(OH)$_2$, —P(O)(OR)(OH), —(P)(OH)$_2$, —OP(O)(R)(OH), and —P(O)(R)(OH), wherein R is a hydrocarbon group that can optionally be substituted.

The phrase "drug depot," as used herein means a precipitate, which includes the compound of formula (I), formed within the body of a treated animal that releases the compound of formula (I) over time.

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than 10% is retained on a 0.22 µm filter when the formulation is filtered through the filter at 98° F. In one embodiment, no more than 5% of the formulation or composition is retained on a 0.22 µm filter when the formulation is filtered through the filter at 98° F. In one embodiment, no more than 2% of the formulation or composition is retained on a 0.22 µm filter when the formulation is filtered through the filter at 98° F. In one embodiment, no more than 1% of the formulation or composition is retained on a 0.22 µm filter when the formulation is filtered through the filter at 98° F.

The phrase "forms a precipitate," as used herein, means that the pharmaceutical composition forms a precipitate, or solid, when injected into water or into a physiological (in vivo) environment. A precipitate is an insoluble solid formed in solution at room temperature in vitro or in a physiological (in vivo) environment. The precipitate can take many forms such as, for example, a solid, a crystal, a gummy mass, or a gel. Preferably, the precipitate is a gummy mass or a gel. A composition of the invention forms a precipitate in water when at least 10% of the composition is retained on a 0.22 µm filter when the composition is mixed with water and filtered at 98° F. Typically, to form the precipitate, about 1 mL of the pharmaceutical composition is injected into about 5 mL of water.

The term "solution," as used herein, means a uniformly dispersed mixture at the molecular or ionic level of one or more substances (solute), in one or more other substances (solvent), typically a liquid.

The Compounds of Formula (I)

The compounds of formula (I) are florfenicol esters. Florfenicol esters are pro-drugs of florfenicol. The compounds of formula (I) have advantageous properties compared to florfenicol and other florfenicol esters.

For example, compound of formula (I), wherein R is —C(O)CH$_2$OCH$_2$CH$_2$OCH$_3$ (formula (Ia)), i.e., the methoxyethoxy acetic acid ester, has a superior pharmacokinetic and pharmacodynamic profile compared to florfenicol and other florfenicol esters when administered by, for example, subcutaneous injection. In particular, the compound of formula (Ia), when administered to an animal by subcutaneous injection, provides a serum concentration of florfenicol that is sufficiently high to be therapeutically effective for a time period that is longer than when either florfenicol or florfenicol butyrate (i.e., the compound of formula (I) wherein R is —C(O)(CH$_2$)$_2$CH$_3$) is administered. Also, the C$_{max}$ for the serum concentration of florfenicol when the compound of formula (Ia) is administered to an animal is lower than the C$_{max}$ for the serum concentration of florfenicol when florfenicol is administered to the animal. A lower C$_{max}$ advantageously avoids undesirable side-effects. Also, it has been observed, by adding the compound of formula (Ia) and florfenicol butyrate to serum in vitro, that the compound of formula (Ia) is hydrolyzed faster than florfenicol butyrate. Therefore, administering the compound of formula (Ia) to an animal will provides a therapeutically effective amount of florfenicol in the serum faster than will be obtained if florfenicol butyrate is administered. The selection of R to be —C(O)CH$_2$OCH$_2$CH$_2$OCH$_3$ advantageously provides a florfenicol ester that has a particularly favorable pharmacokinetic and pharmacodynamic profile compared to florfenicol and other florfenicol esters. In particular, the compound of formula (Ia), when administered to an animal by subcutaneous injection, will be released into the blood stream at a suitable rate, and then hydrolyzed in the blood stream at a sufficient rate, to provide a C$_{max}$ for florfenicol that avoids undesirable side effects and to provide a serum concentration of florfenicol that is therapeutically effective for a longer period of time than obtained by administering florfenicol or other esters of florfenicol.

Similarly, the compound of formula (I), wherein R is —C(O)CH$_2$N(CH$_3$)$_2$ (formula (Ib)), i.e., the dimethylamino glycine ester, also has advantageous properties compared to florfenicol and known florfenicol esters. Specifically, the compound of formula (Ib), having an amino group, can be protonated to provide a salt. Typically, the salt is a pharmaceutically acceptable salt. Salts typically have better solubility in aqueous solvents compared to the neutral compound. Thus, it is expected that the compound of formula (Ib) can be protonated to provide a salt, which would be easier to formulate, especially in aqueous solvents, which are particularly desirable for administration by injection. Furthermore, it is expected that the compound of formula (Ib), like the compound of formula (Ia), when administered to an animal, will show a superior pharmacokinetic and pharmacodynamic profile compared to florfenicol and other florfenicol esters.

In one embodiment, the salt is formed with an inorganic acid.

In one embodiment, the salt is formed with a carboxylic acid. Any carboxylic acid can be used to protonate the compound of formula (Ib). In one embodiment, the carboxylic acid has the formula R$^1$—C(O)OH and R$^1$ is a C$_1$-C$_{22}$ hydrocarbon group. In one embodiment, R$^1$ is a C$_1$-C$_{16}$ hydrocarbon group. In one embodiment, R$^1$ is a C$_6$-C$_{10}$ hydrocarbon group. In one embodiment, R$^1$ is a C$_6$-C$_{16}$ hydrocarbon group. In one embodiment, R$^1$ is a C$_1$-C$_6$ hydrocarbon group. In one embodiment, R$^1$ is a C$_{10}$-C$_{22}$ hydrocarbon group. In one embodiment, R$^1$ is a C$_{10}$-C$_{16}$ hydrocarbon group. In one embodiment, R$^1$ is a C$_{16}$-C$_{22}$ hydrocarbon group.

By appropriate selection of the acid, it is possible to make salts of the compound of formula (Ib) that are soluble in water or insoluble in water. Similarly, by appropriate selection of the acid, it is possible to make salts of the compound of formula (Ib) that are soluble in organic solvents or insoluble in organic solvents.

In yet another embodiment, the compound of formula (Ib) is protonated by an acidic pharmaceutically active compound to provide a salt formed between the compound of formula (Ib) and the acidic pharmaceutically active compound. The resulting salt, thus, contains two pharmaceutically active compounds. Such a composition is advantageous because both pharmaceutically active compounds can be administered simultaneously. For example, bacterial infections are often treated by co-administering an antibacterial agent, such as florfenicol, in conjunction with an anti-inflammatory agent. Many anti-inflammatory agents are acidic (for example, flunixin). Thus, the compound of formula (Ib) could be protonated with an acidic pharmaceutically active compound (for example, an acidic anti-inflammatory, such as flunixin) to provide a salt of the compound of formula (Ib) and the acidic pharmaceutically active compound (for example, an anti-inflammatory, such as flunixin). The resulting salt could then be formulated for administration to an animal to provide a formulation that would enable the co-administration of florfenicol (resulting from the hydrolysis of the compound of formula (Ib)) and the acidic pharmaceutically active compound (for example, an acidic anti-inflammatory, such as flunixin).

The acidic pharmaceutically active compound can be any acidic pharmaceutically active compound.

In one embodiment, the acidic pharmaceutically active compound is an anti-inflammatory selected from aspirin, flunixin, diclofenac, naproxen, ketoprofen, carprofen, and ibuprofen.

In one embodiment, the pharmaceutically active compound is flunixin.

In one embodiment, the pharmaceutically active compound is diclofenac.

In one embodiment, the pharmaceutically active compound is naproxen.

In one embodiment, the pharmaceutically active compound is ketoprofen.

In one embodiment, the pharmaceutically active compound is carprofen.

In one embodiment, the pharmaceutically active compound is ibuprofen.

The compounds of formula (I) can be made by the methods known to those skilled in the art. For example, the compounds of formula (I) can be made by esterifying florfenicol with an acid halide of formula T-C(O)—R, wherein T is a halide, preferably chloride, and R is as defined above, using methods well known to those skilled in the art, such as those described in J. March, *Advanced Organic Chemistry, Reaction Mechanisms and Structure*, 4$^{th}$ ed. John Wiley & Sons, NY, 1992, pp. 393-400.

Acid halides can be obtained using methods well known to those skilled in the art such as those described in J. March, *Advanced Organic Chemistry, Reaction Mechanisms and Structure*, 4$^{th}$ ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with Ph$_3$P in carbon tetrachloride. Acid fluorides can be prepared by reacting a carboxylic acid with cyanuric fluoride.

The compounds of formula (I) can be made according to the method disclosed in US published application no. 2005/0041428, the contents of which are expressly incorporated herein in their entirety.

Pharmaceutical Compositions

The compounds of formula (I) can be combined with one or more additional excipients or additives to provide a dosage form suitable for administration to an animal. When administered to an animal, the compounds of formula (I) are typically administered as a component of a composition that comprises a pharmaceutically acceptable carrier or excipient so as to provide the form for proper administration to the animal. Suitable pharmaceutical excipients are described in *Remington's Pharmaceutical Sciences* 1447-1676 (Alfonso R. Gennaro ed., 19th ed. 1995), incorporated herein by reference. The pharmaceutical compositions can take the form of solutions, suspensions, emulsion, tablets, pills, pellets, capsules, capsules containing liquids, powders, suppositories, emulsions, aerosols, sprays, suspensions, or any other form suitable for use.

In one embodiment, the pharmaceutical compositions are formulated for intravenous, parenteral, or subcutaneous administration. Typically, compositions for intravenous, parenteral, or subcutaneous administration comprise a suitable sterile solvent, which may be an isotonic aqueous buffer or pharmaceutically acceptable organic solvent. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical compositions are to be administered by infusion, they can be dispensed, for example, with an infusion bottle containing, for example, sterile pharmaceutical grade water or saline. Where the pharmaceutical compositions are administered by injection, an ampoule of sterile water for injection, saline, or other solvent, such as a pharmaceutically acceptable organic solvent, can be provided so that the ingredients can be mixed prior to administration.

In one embodiment, the pharmaceutical compositions are formulated with a solvent.

In one embodiment, the solvent is an aqueous solvent.

In one embodiment, the solvent is a pharmaceutically acceptable organic solvent. Suitable pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In one embodiment, the pharmaceutical compositions further comprising a solvent are a solution.

In one embodiment, the pharmaceutical compositions further comprising a solvent are injectable.

In one embodiment, the pharmaceutical compositions further comprising a pharmaceutically acceptable organic solvent form a drug depot when administered to an animal by subcutaneous injection and the drug depot slowly releases the compound of formula (I) over time as described in US published application no. 2005/0041428.

In one embodiment, the pharmaceutical compositions further comprising a pharmaceutically acceptable organic solvent form a precipitate when injected into water.

In another embodiment, the pharmaceutical compositions are formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. Typically, the excipients are of pharmaceutical grade. Orally administered compositions can also contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used.

The pharmaceutical compositions further comprising a solvent can optionally comprise a suitable amount of a pharmaceutically acceptable preservative, if desired, so as to provide additional protection against microbial growth. Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chlorides (e.g., benzethonium chloride).

In one embodiment, any additional components added to the pharmaceutical compositions of the invention are designated as GRAS by the FDA for use or consumption by animals.

In one embodiment, any additional components added to the pharmaceutical compositions of the invention are designated as GRAS by the FDA for use or consumption by humans.

The components of the pharmaceutical composition are preferably biocompatible and non-toxic and, over time, are simply absorbed and/or metabolized by the body.

Methods of Treating a Condition in an Animal

The compounds of formula (I) are useful in human medicine and veterinary medicine. Accordingly, the invention further relates to a method of treating or preventing a condition in an animal comprising administering to the animal an effective amount of a compounds of formula (I). In one embodiment, the condition is a bacterial infection. The compound of formula (I) is typically administered as a pharmaceutical composition comprising the compound of formula (I).

In one embodiment, the invention relates to methods of treating a condition in an animal comprising administering to an animal in need thereof an effective amount of a compound of formula (I).

In one embodiment, the invention relates to methods of preventing a condition in an animal comprising administering to an animal in need thereof an effective amount of compounds of formula (I).

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner. In most instances, administration will result in the release of the compound of formula (I) into the bloodstream and, therefore, the release of florfenicol into the bloodstream.

In one embodiment, the method of treating or preventing a condition in an animal comprises parenterally administering to the animal in need thereof an effective amount of a compound of formula (I). In one embodiment, the compound of formula (I) is administered by infusion or bolus injection. In one embodiment, the compound of formula (I) is administered subcutaneously. In one embodiment, the compound of formula (I) is formulated with a pharmaceutically acceptable organic solvent and is administered by subcutaneous administration to provide a drug depot that slowly releases the compound of formula (I) over time as described in US published application no. 2005/0041428.

In one embodiment, the method of treating or preventing a condition in an animal comprises orally administering to the animal in need thereof an effective amount of a compound of formula (I). In one embodiment, the compound of formula (I) is administered in the form of a capsule or tablet.

The compounds of formula (I) can also be administered by any other convenient route, for example, topically, by absorption through epithelial or mucocutaneous linings (e.g., oral, rectal, and intestinal mucosa, etc.).

The compounds of formula (I) can be administered systemically or locally.

The compounds of formula (I) can be administered together with another biologically active agent.

In one embodiment, the animal is a mammal.
In one embodiment the animal is a human.
In one embodiment, the animal is a non-human animal.
In one embodiment, the animal is a canine.
In one embodiment, the animal is a feline.
In one embodiment, the animal is an equine.
In one embodiment, the animal is a bovine.
In one embodiment, the animal is an ovine.
In one embodiment, the animal is a porcine.

The effective amount administered to the animal depends on a variety of factors including, but not limited to the type of animal being treated, the condition being treated, the severity of the condition, and the specific compound of formula (I) being administered. One of ordinary skill in the art will readily know what is an effective amount of the pharmaceutical composition to treat a condition in an animal.

In one embodiment, a single administration of the compound of formula (I) provides an effective amount of the compound of formula (I). Thus, if the condition is a bacterial infection, the bacterial infection can be treated by administering a single dose of a compound of formula (I).

As discussed above, the compounds of formula (I) have advantageous pharmacodynamic and pharmacokinetic parameters. Accordingly, in one embodiment, the compound of formula (I) is administered to an animal subcutaneously to treat, for example, a bacterial infection, with fewer administrations compared to florfenicol or other esters of florfenicol. In one embodiment, the compound of formula (I) can be administered to an animal to treat, for example, a bacterial infection, with only one injection.

As discussed above, the compound of formula (Ia) has advantageous pharmacodynamic and pharmacokinetic parameters. Accordingly, in one embodiment, the compound of formula (Ia) is administered to an animal subcutaneously to treat, for example, a bacterial infection, with fewer administrations compared to florfenicol or other esters of florfenicol. In one embodiment, the compound of formula (Ia) is administered subcutaneously to an animal to treat, for example, a bacterial infection, with only one injection.

In one embodiment, the compound of formula (Ia), when administered to an animal by subcutaneous injection, provides a $C_{max}$ for florfenicol that is less than when an equivalent amount of florfenicol is administered to the animal by the same route.

In one embodiment, the compound of formula (Ia), when administered to an animal by subcutaneous injection, provides a serum concentration for florfenicol that, 1 day after administration, is higher than if an equivalent amount of florfenicol were administered to the animal by the same route.

In one embodiment, the compound of formula (Ia), when administered to an animal by subcutaneous injection, provides a serum concentration for florfenicol that, 2 days after administration, is higher than if an equivalent amount of florfenicol were administered to the animal by the same route.

In one embodiment, the compound of formula (Ia), when administered to an animal by subcutaneous injection, provides a serum concentration for florfenicol that, 3 days after administration, is higher than if an equivalent amount of florfenicol were administered to the animal by the same route.

In one embodiment, the compound of formula (Ia), when administered to an animal by subcutaneous injection, provides a serum concentration for florfenicol that, 4 days after administration, is higher than if an equivalent amount of florfenicol were administered to the animal by the same route.

In one embodiment, the compound of formula (Ia), when administered to an animal by subcutaneous injection, provides a serum concentration for florfenicol that is greater than 1 µg/mL 2 days after administration.

In one embodiment, the compound of formula (Ia), when administered to an animal by subcutaneous injection, provides a serum concentration for florfenicol that is greater than 1 µg/mL 3 days after administration.

In one embodiment, the compound of formula (Ia), when administered to an animal by subcutaneous injection, provides a serum concentration for florfenicol that is greater than 1 µg/mL 4 days after administration.

Various modifications of the invention in addition to those shown and described herein will become apparent to those skilled in the art and are intended to fall within the scope of the appended claims.

A number of references have been cited, the entire disclosure of which are incorporated herein by reference.

What is claimed is:
1. A compound of formula (I):

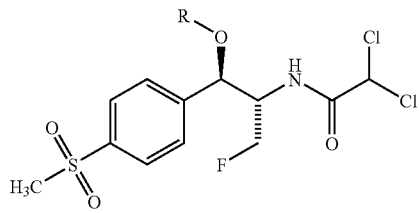

wherein R is —C(O)CH$_2$OCH$_2$CH$_2$OCH$_3$ or —C(O)CH$_2$N(CH$_3$)$_2$.

2. The compound of claim 1, wherein R is —C(O)CH$_2$OCH$_2$CH$_2$OCH$_3$.

3. The compound of claim 1, wherein R is —C(O)CH$_2$N(CH$_3$)$_2$.

4. A composition comprising the compound of claim 3 and an acid in the form of a salt of the compound of formula (I) and the acid.

5. The composition of claim 4, wherein the acid is a carboxylic acid.

6. The composition of claim 4, wherein the acid is a pharmaceutically active acidic compound.

7. A pharmaceutical composition comprising the compound of claim 1 and a pharmaceutically acceptable excipient.

8. A pharmaceutical composition comprising the compound of claim 1 and a pharmaceutically acceptable solvent.

9. The composition of claim 4 further comprising a pharmaceutically acceptable organic solvent.

10. The composition of claim 9, wherein the composition forms a drug depot when administered to an animal by subcutaneous injection.

11. The composition of claim 5, further comprising a pharmaceutically acceptable solvent.

12. The composition of claim 11, wherein the composition forms a drug depot when administered to an animal by subcutaneous injection.

13. The composition of claim 6, further comprising a pharmaceutically acceptable solvent.

14. The composition of claim 13, wherein the composition forms a drug depot when administered to an animal by subcutaneous injection.

15. The pharmaceutical composition of claim 8, wherein the pharmaceutical composition forms a drug depot when administered to an animal by subcutaneous injection.

16. The pharmaceutical composition of claim 8 in the form of a solution.

17. The composition of claim 9 in the form of a solution.

18. The composition of claim 11 in the form of a solution.

19. The composition of claim 13 in the form of a solution.

20. A method of treating or preventing a bacterial infection in an animal comprising administering to an animal in need thereof a compound of claim 1.

* * * * *